United States Patent
Selvin

(10) Patent No.: US 6,667,179 B1
(45) Date of Patent: Dec. 23, 2003

(54) SEMICONDUCTOR LUMINESCENCE QUENCHERS FOR DETECTING PROXIMAL MOLECULAR BINDING EVENTS

(75) Inventor: Paul R. Selvin, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/430,384

(22) Filed: Oct. 28, 1999

(51) Int. Cl.$^7$ .................. G01N 33/557; G01N 33/53
(52) U.S. Cl. .................. 436/517; 435/6; 435/7.1; 436/523; 436/527; 436/537; 436/546; 436/164; 436/165; 436/172; 436/805
(58) Field of Search .................. 435/4, 6, 7.1, 8, 435/7.92, 28, 25, 7.93, 91.1, 91.2, 287.9, 288.2, 288.3, 288.7, 808, 817; 436/517, 523, 527, 537, 546, 164, 166, 172, 829, 805; 422/82.08, 82.11; 385/12, 37, 130, 131; 204/403; 540/450, 451, 452, 55; 536/220.1, 23.1, 24.2, 24.3

(56) References Cited

U.S. PATENT DOCUMENTS

| | | | | |
|---|---|---|---|---|
| 4,713,324 A | * | 12/1987 | Fox et al. ............... | 435/4 |
| 5,156,972 A | * | 10/1992 | Issachar ............... | 435/288 |
| 5,622,821 A | * | 4/1997 | Selvin et al. ............ | 435/6 |
| 5,822,472 A | * | 10/1998 | Danielzik et al. ......... | 385/12 |
| 6,306,610 B1 | * | 10/2001 | Bawendi et al. ......... | 435/7.1 |
| 6,361,944 B1 | * | 3/2002 | Mirkin et al. ............ | 435/6 |

FOREIGN PATENT DOCUMENTS

FI    WO 98/15830    *    4/1998 .................. 435/6

OTHER PUBLICATIONS

Sluch et al., Anomalous distance dependence of fluorescence lifetime quenched by a semiconductor, Physical Letters A200 (1995) 61–64.*

* cited by examiner

*Primary Examiner*—Long V. Le
*Assistant Examiner*—Gailene R. Gabel
(74) *Attorney, Agent, or Firm*—Richard Aron Osman

(57) ABSTRACT

The invention provides methods and compositions for detecting binding or unbinding of a molecule to a substrate. The molecule comprises a luminophore and the substrate comprises a semiconductor which acts as a luminescence quencher to provide distance-dependent quenching of the luminophore. Binding or unbinding of the molecule, which may be covalent or noncovalent, is detected as a decrease or increase, respectively, of the detectable luminescence of the luminophore.

21 Claims, No Drawings

SEMICONDUCTOR LUMINESCENCE QUENCHERS FOR DETECTING PROXIMAL MOLECULAR BINDING EVENTS

FIELD OF THE INVENTION

The field of the invention is the use of semiconductor substrate quenchers of luminescence to detect proximal molecular binding events.

BACKGROUND OF THE INVENTION

Methods for detecting the binding of molecules to surfaces provide applications in numerous industries. For example, surface plasmon resonance has been used to detect molecular binding in a host of chemical and biotechnological fields, e.g. Deckert and Legay, 1999, Anal Biochem 1;274(1):81-9; Gomes et al., 1999, Vaccine, 18, 362–370; and Fierobe et al., 1999, Biochemistry 38, 12822–32.

Among certain physicists and material scientists, it is known that metals and semimetals can function as luminescence quenchers over short distances (see, e.g. Sluch et al., 1995, *Anomalous distance dependence of fluorescence lifetime quenched by a semiconductor*, Physical letters A200 (1995), 61–64). At least two distinct phenomenon are believed to contribute to proximal quenching: first, the excitation intensity is reduced for distances smaller than $\lambda/4$ due to destructive interference of the incoming wave with the partially reflected wave from the surface (e.g. the silicon/silicon oxide boundary of silicon semiconductors); and second, the semiconductor functions as an acceptor by energy transfer. To date, the exploitation of this quenching property has been limited: Walczak et al. examined molecular distances from gold particles (Walczak et al., "*Golden ruler*": *Very long-range resonance energy transfer to surface plasmon acceptors*, 1997, Biophysical Journal, Febuary 1997 Vol. 72, No. 2, Part 2, pp. TU367-TU367) and Nakache et al. measured mobility of a phospholipid in fluorescent recovery after photobleaching (FRAP) experiments (Nakache et al., *Heterogeneity of membrane phospholipid mobility in endothelial cells depends on cell substrate*, 1985, Nature 317, 75–77). In fact, gold particles have been widely used in analytical applications, primarily for its heavy, electron-dense and inert properties, though its usefulness has been limited by the difficulty adhering to it biological molecules (see, e.g. Kramarcy and Sealock, 1991, J. Histochem Cytochem 39, 7–39).

Here we disclose that semiconductor luminescent quenching can be successfully applied to binding assays, and particularly to assaying binding and unbinding of receptor-ligand pairs. Our methods provide exceptionally large $R_q$ (distance at which quenching is 50%) values, e.g. approx. 50 nm, and more. This very large $R_q$ provides significant advantages over conventional fluorescence resonance energy transfer (FRET). For example, even with large receptors, the luminophore-ligand will be highly quenched—in contrast to conventional FRET which does not work well with large biomolecules. In addition, only the ligand need be labeled with luminophore in our technique, whereas in conventional FRET both ligand and receptor need be labeled.

The large $R_o$ also permits a number of hitherto impractical applications. For example, the semiconductor may be coated with a glass layer, a protein layer (e.g. biotinylated bovine serum albumin) can then attached to the glass layer, a second surface which acts as a crosslinker, such as streptavidin, can then be attached thereto, and finally, the biotinylated receptor then attached to the streptavidin. By forming a protein layer between the glass and receptor of interest, the receptor is much more likely to maintain its biological activity, since it is known that interaction with glass often denatures biomolecules.

Our technique also has advantages compared to fluorescence depolarization assays because the latter require that the ligand-bound fluorophore undergo a sizeable change in mobility upon ligand-binding to the receptor. This is often not the case and is difficult to optimize. In our technique, the luminophore's detailed interaction with the ligand and/or receptor is unimportant. The luminophore need only be attached to the ligand and the ligand upon binding to the receptor be brought in reasonably close proximity to the quenching surface.

SUMMARY OF THE INVENTION

The invention provides methods and compositions for detecting binding or unbinding of a molecule to a substrate. The molecule comprises a luminophore and the substrate comprises a semiconductor which acts as a luminescence quencher to provide distance-dependent quenching of the luminophore. Binding or unbinding of the molecule, which may be covalent or noncovalent, is detected as a decrease or increase, respectively, of the detectable luminescence of the luminophore.

The substrate may comprise a wide variety of semiconductors such as silicon, germanium, gallium-arsenide alloys, III/V alloys, etc., and take a wide variety of forms such as crystalline and amorphous materials, micro and nano particle suspensions, etc. The substrate may be coated, derivatized, etc. to provide improved and/or specific binding of the molecule. For example, the substrate may be chemically derivatized with thiol groups or coated with one or more layers of material such as glass, polyethylene glycol (PEG), protein, membrane, etc.

A wide variety of molecules and bindings/unbindings may be detected. In a particular embodiment, the detected binding or unbinding is specifically mediated, such as in a specific molecular binding pair, i.e. ligand and cognate receptor. In a particular aspect of this embodiment, the subject methods involve:

(a) forming a mixture comprising first and second molecules and a substrate, wherein:
the first molecule comprises a luminophore,
one of the first and second molecules is immobilized on the substrate, and
the substrate comprises a semiconductor which acts as a luminescence quencher to provide distance-dependent quenching of the luminophore, and between the semiconductor and the immobilized molecule, a molecular attachment layer,
whereby but for an incubation-induced change in binding of the first and second molecules, the luminophore and substrate are at a reference distance which provides a reference quenching, whereby the mixture provides a reference luminescence, (b) incubating the mixture under conditions wherein the binding of the first and second molecules changes, whereby the luminophore and substrate are at a test distance which provides a test quenching, whereby the mixture provides a test luminescence, and (c) detecting the test luminescence, wherein a difference between the test luminescence and the reference luminescence indicates binding or unbinding of the first and second molecules.

This assay may be constructed in a wide variety of ways with a wide variety of receptor ligand pairs. As examples, the assay encompasses methods wherein:

the forming step, the second molecule is immobilized on the substrate and the first molecule is bound to the second molecule, and wherein the incubating step the first and second molecule unbind, releasing the luminophore from the substrate, e.g. wherein the first molecule is selected from an antigen, cytokine, hormone and a neurotransmitter and the second molecule is a corresponding receptor and optionally, wherein the forming step, the mixture further comprises a modulator which modulates binding of the first and second molecules;

the forming step, the first molecule is immobilized on the substrate and the second molecule is unbound to the first molecule, and wherein the incubating step the first and second molecule bind and release the luminophore from the substrate, e.g. wherein the second molecule is an enzyme selected from a protease, nuclease, helicase, kinase and phosphatase;

the molecular attachment layer comprises a material such as a glass; and the substrate further comprises a phospholipid bilayer between the molecular attachment layer and the immobilized molecule, e.g. wherein the forming step, the immobilized molecule is bound to or in the membrane.

DETAILED DESCRIPTION OF SPECIFIC EMBODIMENTS OF THE INVENTION

The following descriptions of particular embodiments and examples are offered by way of illustration and not by way of limitation. As explained above, the subject binding assays may be constructed in a wide variety of ways with a wide variety of molecular binding pairs.

In a particular aspect of this embodiment, the subject methods involve three steps, (a) forming a mixture comprising first and second molecules and a substrate (b) incubating the mixture under conditions wherein the binding of the first and second molecules changes and (c) detecting a change in luminescence.

The first and second molecule of the mixture may be any binding pair for which binding or unbinding is sought to be determined. The "binding" here encompasses any specific molecular attraction wherein the molecules are brought into close proximity, such as wherein van der Waals forces are operative, and may be covalent or noncovalent, but is generally noncovalent. In addition, the binding may effect a reaction in one of the binding molecules, effecting for example a conformational change, a catalysis such as hydrolysis, phoshphorylation, etc. Exemplary bindings include protein-ligand binding, enzyme-substrate binding, polynucleotide-polynucleotide binding, lipid-lipid hydrophobic binding, etc.

The first molecule comprises a luminophore, which may be a fluorophore and/or a phosphorophore. A wide variety of luminophores are known in the art and include common chemical fluorescers such as fluorescein, fluorescent proteins such as GFP, lanthanide dyes, etc. Techniques for coupling such luminophores to or incorporating such luminophores into a wide variety of target molecules are known in the art.

One of the first and second molecules is immobilized on the substrate. Immobilizing means that the distance between the molecule and the substrate is constrained such that the semiconductor will quench, by at least 25%, preferably by at least 50%, more preferably by at least 75%, the luminophore in the assay. Generally, this distance will be less than about 100 nm, preferably less than about 50 nm, more preferably less than about 25 nm, most preferably less than about 10 nm. A wide variety of methods may be used for immobilizing the molecule. For example, the molecule may be covalently coupled to a chemically derivatized substrate surface, bound to the surface though a high-affinity binding pair reagent (e.g. biotin-streptavidin), contained in or within a lipid bilayer, membrane, gel, etc., etc.

The substrate comprises a semiconductor which acts as a luminescence quencher to provide distance-dependent quenching of the luminophore. A wide variety of semiconductors may be used. Examples include silicon, germanium, gallium-arsenide, indium-arsenide, indium-antimonide alloys, other Ill–V alloys, etc. Essentially any semiconductor with a band gap of less than or equal to about 2 eV may be used. The semiconductor may take a wide variety of forms such as crystalline and amorphous materials, micro and nano particle suspensions (see, e.g. 20–30 nm silicon spheres described in *Transmission electron holography of silicon nanospheres with surface oxide layers*. Applied Physics Letters, Vol. 70, No. 10, Mar. 10, 1997, p. 1296–8), etc., though conventional wafers provide the least expensive material. By quenching is meant that the semiconductor causes a decrease in the intensity and/or excited state lifetime of the luminescense.

The substrate also comprises a molecular attachment layer situated between the semiconductor and the immobilized molecule. This layer insulates the otherwise reactive semiconductor surface and protects the functionality of the binding molecules and/or intermediate compositions otherwise in contact with the semiconductor surface. A wide variety of layers may be used, though the most convenient is often the oxidized form of the semiconductor (e.g. a glass such as silicon dioxide) which may naturally form or be deposited on the surface. Other coating suitable for protecting semiconductor surfaces, e.g. polymeric coatings, are known in the art. In addition, the semiconductor and/or the attachment may be chemically derivatized with various functional groups, such as thiols. Methods for so derivatizing are also known in the art.

The substrate may also comprise one or more additional components situated between the molecular attachment layer and the immobilized molecule, such as assay-inert chemical (e.g. PEG) protein (e.g. BSA) layers, phospholipid bilayer or membranes, cells, which may be lysed, permeablized and/or compressed to provide requisite proximity of the luminophore to the semiconductor, etc. Hence, the immobilized molecule may be embedded in or attached to a bilayer or cell membrane which is coupled to the attachment surface. In a particular embodiment, lysed, permeablized and/or compacted cells provide access to otherwise intracellular receptor domains, such as SH2 domains, which may be assayed for binding. Methods for applying and attaching membranes to attachment surfaces such as glass are well known in the art.

But for an incubation-induced change in binding of the first and second molecules, the luminophore and substrate are at a reference distance which provides a reference quenching, whereby the mixture provides a reference luminescence. The reference luminescence may be measured with the assay mixture, a separate control mixture evaluated in parallel, or may be simply a known or estimated control value. The reference and subsequent test distances, quenchings and luminescences may be considered in terms of individual molecules, but are more conveniently evaluated as aggregate means.

The second and third steps of the method involves incubating the mixture under conditions wherein the binding of the first and second molecules changes, whereby the luminophore and substrate are at a test distance which provides a test quenching, whereby the mixture provides a test luminescence, and detecting the test luminescence, wherein a difference between the test luminescence and the reference luminescence indicates binding or unbinding of the first and second molecules. The incubation conditions are determined empirically, depending on the reagents used. Similarly, any convenient detection method may be used, particularly automated luminometers.

The assay may be constructed in a wide variety of ways with a wide variety of first and second molecular pairs.

In one particular embodiment, the assay encompasses methods wherein the forming step, the second molecule is immobilized on the substrate and the first molecule is bound to the second molecule, and wherein the incubating step the first and second molecule unbind, releasing the luminophore from the substrate. For example, the first molecule may be a ligand such as an antigen, cytokine, hormone and a neurotransmitter and the second molecule may be a corresponding receptor. In particular aspects of this embodiment, the mixture further comprises a modulator which modulates binding of the first and second molecules. For example, the mixture may comprise known or candidate inhibitors, enhancers, activators, agonists, antagonists, etc. of an evaluated binding pair (e.g. receptor-ligand) interaction.

In another particular embodiment, the assay encompasses methods wherein the forming step, the first molecule is immobilized on the substrate and the second molecule is unbound to the first molecule, and wherein the incubating step the first and second molecule bind and release the luminophore from the substrate. For example, the second molecule may be an enzyme selected from a ribozyme, protease, nuclease, helicase, kinase and phosphatase and the first molecule is a corresponding substrate.

EXAMPLES

Example 1. Enzymatic cleavage of luminescently labeled DNA results in release of luminophore from a surface and increase in luminescence. In this demonstration, a luminescently-labeled DNA molecule is bound to a quenching surface, and the cleavage of this DNA by an enzyme enables the luminophore to diffuse away from the surface and luminesce. The increase in luminescence with time is therefore a monitor of nuclease activity.

All luminescent intensities examined are the result of photon counting over a 4 second integration time. The substrate is prepared by adsorbing biotinylated bovine serum albumin directly onto the silicon dioxide layer of the silicon surface. Biotinylated 20 mer DNA is attached to this surface via a streptavidin linker. The sample is prepared at time t=0 and the EcoRI endonuclease is introduced at t=75 minutes. The resulting digestion of the DNA liberates the fluorescein labeled DNA fragment from the quenching support and luminescence increases as the reaction progresses. The data demonstrate a steady background signal for over one hour before the introduction of EcoRI. Therefore the large rise in signal after introduction of EcoRI is caused by enzymatic cleavage of the luminescently labeled DNA, allowing the luminophore to diffuse away from the substrate and luminesce.

The final concentration of fluorescein-DNA digested off the silicon substrate in the above demonstration is approximately 7 nM. This value comes from comparing the intensity of the luminecence following DNA digestion to that of reference solutions containing well defined concentrations of fluorescein-DNA To further demonstrate that EcoRI digests DNA that has been immobilized with our protocol and to obtain a measure of the efficiency of that digestion, we studied the enzyme reaction with a non-quenching glass substrate. Any luminescence remaining on the glass following enzymatic activity and washing is indicative of DNA that was not accessible to the enzyme. The DNA was immobilized on a glass slide as above and the luminescence intensity was measured to be 753 thousand photon counts. Then EcoRI was added to the preparation and allowed to digest for the interval of the experiment shown above, 70 minutes. Then the substrate was washed, removing fluophores that are not bound to the surface. The intensity was then measured to be 272 thousand photon counts. Background signal for the experiment was 81 thousand counts. Hence, approximately ¾ of the DNA is liberated from the substrate via enzyme activity.

Example 2. Enzymatic release of luminescently labeled DNA results in release of luminophore from surface and increase in luminescence. In this demonstration, a luminescently-labeled DNA probe is hybridized to an oligonucleotide which is bound to a quenching surface, and the unwinding of the probe by a helicase enables the luminophore to diffuse away from the surface and luminesce. Suitable solid phase helicase assay conditions are described in U.S. Pat. No. 5,958,696 The increase in luminescence with time is therefore a monitor of helicase activity.

Example 3. Protease cleavage of luminescently labeled protease substrate results in release of luminophore from surface and increase in luminescence. In this demonstration, a luminescently-labeled peptide molecule is bound to a quenching surface, and the cleavage of this peptide by a protease enables the luminophore to diffuse away from the surface and luminesce. Suitable HIV protease assay conditions are described by Kiso, Biopolymers 1996;40(2):235-44. The increase in luminescence with time is therefore a monitor of protease activity.

Example 4. Antibody-Antigen dissociation results in release of luminophore from surface and increase in luminescence. In this demonstration, a luminescently-labeled antigen is bound to an antibody which is immobilized on a quenching surface. The competitive dissociation of the antigen by an agonist enables the luminophore to diffuse away from the surface and luminesce. Suitable immunoassay conditions are widely known in the art. The increase in luminescence with time is therefore a monitor of affinity of the agonist for the antibody.

Example 5. Ligand dissociation results in release of luminophore from surface-bound membrane and increase in luminescence. In this demonstration, a luminescently-labeled ligand is bound to a membrane bound receptor which is immobilized in a membrane layered on a quenching surface. The dissociation of the ligand by an antagonist enables the luminophore to diffuse away from the surface and luminesce. Suitable membrane-bound receptor ligand dissociation assay conditions are widely known in the art. The increase in luminescence with time is therefore a monitor of affinity of the antagonist for the antibody.

All publications and patent applications cited in this specification and all references cited therein are herein incorporated by reference as if each individual publication or patent application or reference were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting binding or unbinding of first and second molecules, said method comprising the steps of
   (a) forming a mixture comprising a first molecule, a second molecule and a substrate, wherein:
   the first molecule comprises a luminophore,
   one of the first and second molecules is immobilized on the substrate, and
   the substrate comprises a semiconductor which acts as a luminescence quencher to provide distance-dependent quenching of the luminophore, and between the semiconductor and the immobilized molecule, a molecular attachment layer,
   whereby but for an incubation-induced change in binding of the first and second molecules, the luminophore and substrate are at a reference distance which provides a reference quenching, whereby the mixture provides a reference luminescence,
   (b) incubating the mixture under conditions wherein the binding of the first and second molecules changes, whereby the luminophore and substrate are at a test distance which provides a test quenching, whereby the mixture provides a test luminescence,
   (c) detecting the test luminescence, wherein a difference between the test luminescence and the reference luminescence indicates binding or unbinding of the first and second molecules,
   wherein the semiconductor has a band gap of less than or equal to about 2 eV and is selected from silicon and germanium, and the substrate is a wafer of the semiconductor.

2. The method of claim 1:
   wherein the forming step, the second molecule is immobilized on the substrate and the first molecule is bound to the second molecule, and
   wherein the incubating step the first and the second molecule unbind, releasing the luminophore from the substrate.

3. The method of claim 2, wherein the semiconductor is silicon.

4. The method of claim 2, wherein the luminophore comprises a lanthanide dye.

5. The method of claim 2, wherein the molecular attachment layer comprises a glass, the semiconductor is silicon and the luminophore comprises a lanthanide dye.

6. The method of claim 1:
   wherein the forming step, the second molecule is immobilized on the substrate and the first molecule is bound to the second molecule, and
   wherein the incubating step the first and the second molecule unbind, releasing the luminophore from the substrate,
   wherein the first molecule is selected from the group consisting of an antigen, cytokine, hormone and a neurotransmitter and the second molecule is a corresponding receptor.

7. The method of claim 1:
   wherein the forming step, the second molecule is immobilized on the substrate and the first molecule is bound to the second molecule, and
   wherein the incubating step the first and the second molecule unbind, releasing the luminophore from the substrate,
   wherein the first molecule is selected from the group consisting of an antigen, cytokine, hormone and a neurotransmitter and the second molecule is a corresponding receptor,
   wherein the forming step, the mixture further comprises a modulator which modulates binding of the first and second molecules.

8. The method of claim 1:
   wherein the forming step, the first molecule is immobilized on the substrate and the second molecule is unbound to the first molecule, and
   wherein the incubating step the first and the second molecule bind and release the luminophore from the substrate.

9. The method of claim 8, wherein the semiconductor is silicon.

10. The method of claim 8, wherein the luminophore comprises a lanthanide dye.

11. The method of claim 8, wherein the molecular attachment layer comprises a glass, the semiconductor is silicon and the luminophore comprises a lanthanide dye.

12. The method of claim 1:
    wherein the forming step, the first molecule is immobilized on the substrate and the second molecule is unbound to the first molecule, and
    wherein the incubating step the first and the second molecule bind and release the luminophore from the substrate,
    wherein the second molecule is an enzyme selected from the group consisting of a protease, nuclease, helicase, kinase and phosphatase.

13. The method of claim 1 wherein the molecular attachment layer comprises a glass.

14. The method of claim 13, wherein the semiconductor is silicon.

15. The method of claim 13, wherein the luminophore comprises a lanthanide dye.

16. The method of claim 1 wherein the substrate further comprises a phospholipid bilayer between the molecular attachment layer and the immobilized molecule.

17. The method of claim 16, wherein the semiconductor is silicon.

18. The method of claim 16, wherein the luminophore comprises a lanthanide dye.

19. The method of claim 1 wherein the substrate further comprises a phospholipid bilayer between the molecular attachment layer and the immobilized molecule, and wherein the forming step, the immobilized molecule is bound to or in the bilayer.

20. The method of claim 1, wherein the semiconductor is silicon.

21. The method of claim 1, wherein the luminophore comprises a lanthanide dye.

* * * * *